(12) United States Patent
Hestdal

(10) Patent No.: US 10,556,010 B2
(45) Date of Patent: Feb. 11, 2020

(54) NEOADJUVANT THERAPY FOR BLADDER CANCER

(71) Applicant: PHOTOCURE ASA, Oslo (NO)

(72) Inventor: Kjetil Hestdal, Oslo (NO)

(73) Assignee: PHOTOCURE ASA, Oslo (NO)

( * ) Notice: Subject to any disclaimer, the term of this patent is extended or adjusted under 35 U.S.C. 154(b) by 0 days.

(21) Appl. No.: 16/063,185

(22) PCT Filed: Dec. 19, 2016

(86) PCT No.: PCT/EP2016/081803
§ 371 (c)(1),
(2) Date: Jun. 15, 2018

(87) PCT Pub. No.: WO2017/103283
PCT Pub. Date: Jun. 22, 2017

(65) Prior Publication Data
US 2018/0369379 A1  Dec. 27, 2018

(30) Foreign Application Priority Data
Dec. 17, 2015 (GB) .................................. 1522309.2

(51) Int. Cl.
| | | |
|---|---|---|
| A61K 41/00 | (2006.01) |
| A61K 9/00 | (2006.01) |
| A61K 9/08 | (2006.01) |
| A61K 39/395 | (2006.01) |
| A61K 47/02 | (2006.01) |
| A61N 5/06 | (2006.01) |

(52) U.S. Cl.
CPC ........ *A61K 41/0061* (2013.01); *A61K 9/0034* (2013.01); *A61K 9/08* (2013.01); *A61K 39/3955* (2013.01); *A61K 47/02* (2013.01); *A61N 5/062* (2013.01); *A61N 2005/061* (2013.01); *A61N 2005/0629* (2013.01); *A61N 2005/0663* (2013.01)

(58) Field of Classification Search
CPC .................................................. A61K 41/0061
USPC ........................................................ 514/551
See application file for complete search history.

(56) References Cited

U.S. PATENT DOCUMENTS

2006/0110383 A1   5/2006   Honjo et al.

FOREIGN PATENT DOCUMENTS

| WO | 1996/028412 A1 | 9/1996 |
|---|---|---|
| WO | 2004/004771 A1 | 1/2004 |
| WO | 2005-092838 A1 | 10/2005 |
| WO | 2008/156712 A1 | 12/2008 |
| WO | 2009114335 A2 | 9/2009 |
| WO | 2010/077634 A1 | 7/2010 |
| WO | 2010/142457 A1 | 12/2010 |
| WO | 2013/019906 A1 | 2/2013 |
| WO | 2013/079174 A1 | 6/2013 |
| WO | 2013/181452 A1 | 12/2013 |

OTHER PUBLICATIONS

Baglo et al., "Photodynamic therapy with hexyl aminolevulinate induces carbonylation, posttranslational modifications and changed expression of proteins in cell survival and cell death pathways", Photochemical & Photobiological Sciences, vol. 10, No. 7, pp. 1137-1145 (2011).*
Rink, M. et al., "Hexyl Aminolevulinate-Guided Fluorescence Cystoscopy in the Diagnosis and Follow-up of Patients with Non-Muscle-Invasive Bladder Cancer: A Critical Review of the Current Literature"; European Urology (2013); vol. 64; pp. 624-638.
Witjes, J. A. et al., "Clinical and Cost Effectiveness of Hexaminolevulinate-guided Blue-light Cystoscopy: Evidence Review and Updated Expert Recommendations"; European Urology (2014: vol. 66; pp. 863-871.
Gakis, G. et al., "Photodynamic Diagnosis-guided TUR-BT is an Independent Predictor for Improved Recurrence-free Survival after Radical Cystectomy for Invasive Bladder Cancer"; Urology (2013); vol. 82 (3 Supplemental 1); pp. S208; Abstract No. UP.046.
Bader, M. J. et al., "Photodynamic Therapy of Bladder Cancer—A Phase I Study Using Hexaminolevulinate (HAL)"; Urologic Oncology (2013); vol. 31, pp. 1178-1183.
Sundarararajan, S. et al., "Anti-PD-1 and PDL1 Therapy for Bladder Cancer: What is on the Horizon"; Future Oncology (2015); vol. 11:16; pp. 2299-2306.

* cited by examiner

*Primary Examiner* — Kevin E Weddington
(74) *Attorney, Agent, or Firm* — Fox Rothschild LLP

(57) ABSTRACT

This invention relates to a neoadjuvant therapy for bladder cancer in bladder cancer patients who are scheduled for a cystectomy and methods of carrying out such a neoadjuvant therapy. In particular the invention relates to a composition comprising hexyl 5-ALA ester (HAL) or a pharmaceutically acceptable salt thereof for use in a neoadjuvant therapy for bladder cancer in a bladder cancer patient who is scheduled for a cystectomy, the therapy comprises instilling said composition into the bladder of said patient and exposing the inside of said bladder to light.

18 Claims, No Drawings

NEOADJUVANT THERAPY FOR BLADDER CANCER

This invention relates to a neoadjuvant therapy for bladder cancer in bladder cancer patients who are scheduled for a cystectomy and methods of carrying out such a neoadjuvant therapy.

Bladder cancer is the ninth most common cancer diagnosis worldwide, with more than 330000 new cases each year and more than 130000 deaths per year. At any point in time, 2.7 million people have a history of urinary bladder cancer.

The diagnosis of bladder cancer ultimately depends on cystoscopic examination of the bladder (cystoscopy) and histological evaluation of the resected tissue. In general, cystoscopy is initially performed in the office, using flexible instruments. At the initial diagnosis of bladder cancer, 70% of cases are diagnosed as non-muscle-invasive bladder cancer (NMIBC) and approximately 30% as muscle-invasive bladder cancer (MIBC).

If a bladder tumor has been detected during cystoscopy, the patient will undergo transurethral resection (TUR), i.e. a procedure where the bladder is visualized through the urethra and tumors and lesions are resected. In case of NMIBC, such a resection is to completely remove the tumor while in case of MIBC, such a resection is of a palliative nature. Apart from the resection of the tumor, the TUR is also carried out to enable a correct histological diagnosis of the resected tumor/tumor biopsies by a pathologist.

For patients with MIBC, the standard treatment is radical cystectomy, i.e. removal of the bladder and adjacent organs, that is prostate and seminal vesicles in men, and uterus and adnexa in women. It also includes the dissection of regional lymph nodes. Cystectomy is also advocated in patients with NMIBC who are at high risk of progression, i.e. patients having multiple recurrent high-grade tumors, high-grade T1 tumors or high-grade tumors with concurrent carcinoma-in-situ (CIS). Further, cystectomy is advocated in patients with NMIBC who have received Bacillus Calmette-Guérin (BCG) immunotherapy but where such treatment has failed.

Although being the gold standard for MIBC treatment and advocated in patients with certain types of NMIBC, radical cystectomy only provides for 5-year survival in about 50% of the patients. In order to improve these unsatisfactory results, the use of neoadjuvant therapies, i.e. therapies before/prior to the main treatment cystectomy, has been explored since the 1980s.

Neoadjuvant radiotherapy has been used but down staging of the cancer after such radiotherapy takes about 4-6 weeks. Moreover, a delay of surgery in patients with locally advanced bladder cancer beyond 90 days has shown to cause a significant increase in extravesical disease (81 vs 52%). Neoadjuvant radiotherapy is not recommended according to the current European guidelines on MIBC since no data exist to support that neoadjuvant radiotherapy for operable MIBC increases survival.

Neoadjuvant chemotherapy has many advantages including that chemotherapy is delivered at the earliest time-point, when the burden of micrometastatic disease is expected to be low; that tolerability of chemotherapy is expected to be better before cystectomy rather than after; and hypothetically that patients with micrometastatic disease might respond to neoadjuvant therapy and thus reveal favorable pathological status determined mainly by negative lymph node status and negative surgical margins. Neoadjuvant cisplatin-containing chemotherapy has shown to significantly improve survival (5% absolute improvement in survival at 5 years). However, as stated above, delayed cystectomy may compromise the outcome in patients who are not sensitive to chemotherapy and generally, pre-operative anemia and neuropathy is more common in patients receiving neoadjuvant chemotherapy prior to cystectomy. The current European guidelines on MIBC state that " . . . neoadjuvant chemotherapy has its limitations regarding patient selection, current development of surgical technique, and current chemotherapy combinations." Hence, there is room for improvement of neoadjuvant therapies for bladder cancer patients who are scheduled for a cystectomy.

We therefore suggest that a bladder cancer patient scheduled for a cystectomy receives neoadjuvant therapy comprising the instillation into the bladder of said patient of a composition comprising hexyl 5-ALA ester (HAL) or a pharmaceutically acceptable salt thereof and exposing the inside of said bladder to light.

In bladder cancer management, instillation into the bladder of a patient of a composition comprising HAL or a pharmaceutically acceptable salt thereof and exposing the inside of said bladder to blue light may be used to improve visualization of bladder cancer during cystoscopy and/or TUR. As a standard procedure, cystoscopy and TUR are performed using white light. However, since the use of white light can lead to missing lesions that are present but not visible, photodynamic diagnosis (PDD) is often used in such procedures. PDD involves the administration of a photosensitizer or a precursor thereof (i.e. a "photosensitizing agent") to an area of interest. The photosensitizer or precursor thereof is taken up into the cells, where a precursor of a photosensitizer is converted into an active photosensitizer. Upon exposure of the area of interest to light of a suitable wavelength, the photosensitizer is excited and, upon relaxation to its ground state, fluorescence occurs.

Hexyl 5-ALA ester (hexaminolevulinate, HAL) and its salts are such photosensitizing agents. HAL preferably penetrates rapidly proliferating cells, e.g. tumor cells, where it is converted into porphyrins, which are photosensitizers and fluorescent compounds. Under subsequent blue-light illumination, the porphyrins emit red light and thus enable specific and accurate visualization of the tumor. Hexvix® (Photocure ASA, Norway and Ipsen SA, France) is a commercially available approved drug that comprises HAL and is used in PDD in cystoscopy and TUR procedures.

In patients with NMIBC, HAL-guided cystoscopy and TUR has improved detection of both papillary tumors and flat carcinoma-in-situ (CIS) lesions, the latter of which are difficult to detect with white light alone. HAL-guided TUR of bladder cancer in patients with NMIBC has further reduced the rate of residual tumor after such procedures and has led to superior recurrence free survival (RFS) rates and prolonged RFS intervals compared to white light TUR alone (see Rink M, et al. Eur Urol 4(64), 2013, 624). Existing European guidelines on NMIBC and several expert groups consensus statements recommend the use of HAL-guided TUR in various settings of management of NMIBC and some even recommend its use in all NMIBC patients at initial TUR (see Witjes J A, et al., Eur Urol 1(66), 2014, 863).

Also in patients with MIBC, HAL-guided TUR impacts recurrence free survival: in 268 consecutive patients who had cystectomy, it was retrospectively investigated whether patients prior to the cystectomy had undergone HAL-guided TUR or whether TUR was carried out with white light alone. Kaplan-Meier analysis was used to estimate recurrence-free survival (RFS) and overall survival (OS). The 3-year RFS was 69.8% in patients with HAL-guided TUR and 58.2% in patients with white light TUR alone. The 3-year OS was 65.0% in patients with HAL-guided TUR and 56.6%. These results indicate that HAL-guided TUR is associated with improved RFS after cystectomy in patients with MIBC (see G. Gakis et al., Urology Vol. 82, Issue 3, Supplement, Unmoderated Posters, UP.046).

The rate of residual tumor and detection of all tumor lesions in the bladder during TUR performed in patients with MIBC is not an issue, since the bladder is removed in its entirety anyway. Hence, TUR in patients with MIBC is usually performed with white light alone and there is no guideline recommendation of using HAL-guidance under such TURs.

Clearly, in view of its current use in the management of bladder cancer, it is surprising that HAL can be used as a neoadjuvant therapy for bladder cancer patients who are scheduled for a cystectomy.

HAL has several advantages compared to the neoadjuvant radiotherapy or chemotherapy mentioned above, where nausea, vomiting, fatigue, anemia, damage to epithelial surfaces, intestinal discomfort/gastrointestinal stress, nephrotoxicity, neurotoxicity, swelling, depression of the immune system and infertility are well-known and common adverse effects. In contrary thereto, most of the reported adverse reactions to HAL (in the form of Hexvix®) were transient and mild or moderate in intensity. The most frequently reported adverse reactions from clinical studies with Hexvix® were bladder spasms, reported by 2.4% of the patients, dysuria (1.8%), bladder pain (1.7%) and hematuria (1.7%).

Further, HAL has a highly favorable metabolic profile compared to neoadjuvant chemotherapeutics, e.g. cisplatin. HAL interferes with the body's own heme biosynthetic pathway and leads of accumulation of photoactive porphyrins, particularly protoporphyrin IX (PpIX), the last intermediate in heme synthesis. Since such photoactive porphyrins are compounds which naturally occur in the body, there is a "natural process" in the body for degrading (metabolizing) and excreting degraded heme.

Hence in a first aspect the invention provides a neoadjuvant therapy for bladder cancer in a bladder cancer patient who is scheduled for a cystectomy, said therapy comprises instilling into the bladder of said patient a composition comprising hexyl 5-ALA ester (HAL) or a pharmaceutically acceptable salt thereof and exposing the inside of said bladder to light.

In an alternative first aspect, the invention provides a composition comprising hexyl 5-ALA ester (HAL) or a pharmaceutically acceptable salt thereof for use in a neoadjuvant therapy for bladder cancer in a bladder cancer patient who is scheduled for a cystectomy, the therapy comprises instilling said composition into the bladder of said patient and exposing the inside of said bladder to light.

The bladder cancer in the context of the invention is either muscular invasive bladder cancer (MIBC) or non-muscular invasive bladder cancer (NMIBC). In the latter case, the NMIBC is one with a high risk of progression, including multiple recurrent high-grade tumors or high-grade T1 tumors or high-grade tumors with concurrent carcinoma-in-situ (CIS).

The term "neoadjuvant therapy" means the administration of a therapeutic agent before/prior to the main treatment for the disease. In the context of the invention, the main treatment is cystectomy and the disease is bladder cancer, i.e. MIBC or NMIBC.

The term "5-ALA" denotes 5-aminolevulinic acid, i.e. 5-amino-4-oxo-pentanoic acid.

The term "hexyl 5-ALA ester" (HAL) denotes n-hexyl aminolevulinate, i.e. n-hexyl 5-amino-4-oxo-pentanoate.

The term "pharmaceutically acceptable salt" denotes a salt that is suitable for use in the dry pharmaceutical product and which fulfils the requirements related to for instance safety, bioavailability and tolerability (see for instance P. H. Stahl et al. (eds.) Handbook of Pharmaceutical Salts, Publisher Helvetica Chimica Acta, Zurich, 2002). The synthesis of hexyl 5-ALA ester is known in the art and may be prepared as described in e.g. WO 96/28412, the entire contents of which are incorporated herein by reference. Briefly, hexyl 5-ALA ester may be prepared by reaction of 5-ALA with hexanol in the presence of a catalyst, e.g. an acid. Further, hexyl 5-ALA ester hydrochloride is commercially available, e.g. in the form of Hexvix® (Photocure ASA and Ipsen Pharma SA) or Cysview® (Photocure Inc.).

The hexyl 5-ALA ester for use in embodiments of the invention is preferably in the form of a pharmaceutically acceptable salt. Such salts are preferably acid addition salts with pharmaceutically acceptable organic or inorganic acids. Suitable acids include, for example, hydrochloric, nitric, hydrobromic, phosphoric, sulfuric, sulfonic acid and sulfonic acid derivatives, the salts of ALA-esters and the latter acids are described in WO 2005/092838 to Photocure ASA, the entire contents of which are incorporated herein by reference. A preferred acid is hydrochloride acid, HCl. Synthetic procedures for salt formation are conventional in the art and are for instance described in WO 2005/092838.

The concentration of HAL in the composition for use in the invention is conveniently in the range of 0.1 to 5% by weight of the total weight of the composition or the equivalent concentration of a pharmaceutically acceptable salt of HAL, preferably 0.15 to 3.5%, and most preferably 0.17% (e.g. corresponding to 0.2% HAL hydrochloride).

The composition for use in the invention may comprise pharmaceutically acceptable carriers, excipients, or stabilizers. The composition for use in the invention is preferably a semi-solid composition or a liquid composition. The term "semi-solid" denotes a physical state which is neither solid nor liquid. Semi-solids (or quasi-solids) are similar to a solid in some respects, e.g. a semi-solid can support its own weight and hold its shape but also shares some properties of liquids, such as shape conformity to something applying pressure to it, or the ability to flow under pressure. Semi-solids are characterized by a three-dimensional structure that is sufficient to impart solid-like character to the undisturbed system but that is easily broken down and realigned under an applied force. Semi-solids have a rigidity and viscosity intermediate between a solid and a liquid. Preferred semi-solid compositions are foams, gels and lotions, preferably low viscosity gels and lotions. However, liquid compositions are preferred, especially liquid compositions that are solutions or suspensions of HAL in a liquid carrier. Preferred liquid carriers are water or aqueous solutions, most preferred liquid carriers are aqueous buffers.

The composition for use in the invention may contain pharmaceutically acceptable excipients including emulsifiers, mucoadhesives, surface penetration agents or chelating agents (see for instance WO 2010/142457).

In a preferred embodiment, the composition for use in the invention is a liquid composition comprising a liquid carrier, more preferably water or an aqueous solution and most preferably an aqueous buffer, preferably a phosphate buffer. In a particularly preferred embodiment, the composition for use in the invention comprises as a liquid carrier an aqueous phosphate buffer, more preferably a phosphate buffer comprising disodium phosphate dehydrate, potassium dihydrogen phosphate, sodium chloride, hydrochloric acid, sodium hydroxide and water.

In a particularly preferred embodiment, the composition for use of the invention is Hexvix®, i.e. a dissolution of hexyl 5-ALA ester hydrochloride (2 mg/ml; 0.2%) in an aqueous buffer comprising disodium phosphate dehydrate, potassium dihydrogen phosphate, sodium chloride, hydrochloric acid, sodium hydroxide and water.

In a preferred embodiment, the HAL or the pharmaceutically acceptable salt thereof is provided in a lyophilized form, and is reconstituted in a liquid carrier, preferably in water or an aqueous solution, most preferably in an aqueous buffer, prior to use.

If the composition for use in the invention is a liquid composition comprising water, the pH of said composition is preferably in the range of 4.5 to 7.5, more preferably a pH in the range of 5.7 to 7.2.

The amount of the composition, which is instilled into the bladder, may vary according to the bladder volume and size of the bladder of the patient. In general, and as observed in the use of Hexvix®, a volume of about 50 ml of the composition is suitable and sufficient.

The composition for use in the invention is preferably instilled into the empty bladder through a catheter, preferably a catheter which is part of a cystoscope, and is left in the bladder from about 20 minutes to about 3 hours, more preferably from about 30 minutes to about 2 hours, most preferably no less than 1 hour, e.g. 1 hour. If the patient cannot retain the composition for 1 hour, at least 1 hour should be allowed to pass from the instillation of the composition into the bladder to the start of exposing the inside of the bladder to light.

For exposing the inside of the bladder to light, any wavelength of light which is suitable to excite the hexyl 5-ALA ester may be used. Preferred is white light, i.e. visible light with wavelengths of from about 350 to 700 nm and/or blue light, i.e. wavelengths of from about 360 nm to about 450 nm and/or red light, i.e. wavelengths of from about 600 to 670 nm. The term "and/or" means that e.g. the inside of the bladder is exposed to either white or blue light or to white light and blue light, subsequently and not at the same time. Especially preferred is white light and/or blue light, more preferred white light followed by blue light. Thus, in one embodiment, the inside of the bladder is first exposed to white light and then subsequently exposed to blue light.

In a preferred first embodiment, the neoadjuvant therapy of the invention comprises a) instilling Hexvix®, i.e. a dissolution of hexyl 5-ALA ester hydrochloride (2 mg/ml; 0.2%) in an aqueous buffer comprising disodium phosphate dehydrate, potassium dihydrogen phosphate, sodium chloride, hydrochloric acid, sodium hydroxide and water into the bladder of a patient who is scheduled for a cystectomy, preferably at a volume of 50 ml and b) exposing the inside of the bladder to white light and then subsequently to blue light.

In an alternative preferred first embodiment, the invention provides Hexvix®, i.e. a dissolution of hexyl 5-ALA ester hydrochloride (2 mg/ml; 0.2%) in an aqueous buffer comprising disodium phosphate dehydrate, potassium dihydrogen phosphate, sodium chloride, hydrochloric acid, sodium hydroxide and water for use in a neoadjuvant therapy for bladder cancer in a bladder cancer patient who is scheduled for a cystectomy, the therapy comprises a) instilling Hexvix® into the bladder of said patient and b) exposing the inside of said bladder white light and then subsequently to blue light.

For exposing the inside of the bladder to light, approved cystoscopic light sources are preferred which allow both for white light and blue light irradiation of the inside of the bladder. Such cystoscopes are commercially available, e.g. from Karl Storz (Photodynamic Diagnostic D-Light C (PDD) System), Olympus or Richard Wolf). For red light irradiation, such equipment may be modified with the suitable filters. Such cystoscopic light sources may be rigid or flexible.

The light dose given during irradiation of the inside of the bladder with use of white and blue light may vary but is preferably 0.01 to 100 $J/cm^2$, more preferably 0.03–40 $J/cm^2$ and most preferably 0.1 to 3 $J/cm^2$. For a cystoscopic light source with a output in the range of 47-82 mW such a light dose is provided in about 10 to 30 minutes (calculated based on a 300 $cm^2$ surface area for a human bladder).

The time between the neoadjuvant therapy of the invention, i.e. instillation into the bladder of a composition comprising HAL and exposing the inside of said bladder to light and the cystectomy may vary but is preferably zero to 6 weeks, e.g. zero to 1, 2, 3, 4, 5 or 6 weeks, and more preferably zero to 3 weeks, e.g. 1 or 2 weeks. "Zero" means that the cystectomy is carried out directly after the light irradiation provided in the neoadjuvant method of the invention is finalized. This has the advantage that the patient is only anaesthetized once.

The neoadjuvant therapy of the invention may be carried out once or repeatedly prior to the cystectomy, i.e. carried out two or more times, e.g. 3, 4, 5 or 6 times, with a period between the treatments of e.g. 4 days to 4 weeks, e.g. 1, 2 or 3 weeks.

The neoadjuvant therapy of the invention may be carried out prior, simultaneously or after other neoadjuvant therapies, including neoadjuvant radiotherapy, neoadjuvant chemotherapy (intravescial instillation or systemic administration) with e.g. cisplatin, methotrexate, vinblastine, valurubicin, adriamycin, mitomycin C or combinations thereof and neoadjuvant immunotherapy (intravescial instillation or systemic administration) with e.g. BCG.

A preferred neoadjuvant immunotherapy which may be carried out prior, simultaneously or after the neoadjuvant therapy of the invention includes the use of anti-PD-L1 antibodies. Anti-PD-L1 is an investigational monoclonal antibody designed to interfere with a protein called PD-L1. Anti-PD-L1 targets PD-L1 expressed on cancer cells and tumor-infiltrating immune cells, preventing it from binding to PD-1 and B7.1 on the surface of T cells. By inhibiting PD-L1, anti-PD-L1 may enable the activation of T cells, restoring their ability to effectively detect and attack cancer cells, e.g. bladder cancer cells.

Another preferred neoadjuvant immunotherapy which may be carried out prior, simultaneously or after the neoadjuvant therapy of the invention includes the use of anti-PD-1 antibodies. Anti-PD-1 is an investigational monoclonal antibody that binds to the PD-L1 (programmed death-ligand 1) protein, which is present at high levels in many cancer types, e.g. bladder cancer. By competitively blocking the interaction with PD-1 receptors, it is believed that anti-PD-1 thereby restores anti-cancer T-cell responses.

Thus, anti-PD-L1 antibodies and anti-PD-1 antibodies target different components of the same interaction mechanism between immune cells (specifically killer T cells) and cancer cells, but have a similar therapeutic effect: anti-PD-L1 antibodies target PD-L1 (programmed death ligand-1)

expressed on cancer cells while anti-PD-1 antibodies target the other half of this mechanism, PD-1 (programmed death receptor-1), which is expressed on killer T cells.

In a second aspect, the invention provides a neoadjuvant therapy for bladder cancer in a bladder cancer patient who is scheduled for a cystectomy, said therapy comprises a) instilling into the bladder of said patient of a composition comprising hexyl 5-ALA ester (HAL) or a pharmaceutically acceptable salt thereof and exposing the inside of said bladder to light and b) instilling into the bladder of said patient of a composition comprising anti-PD-L1 antibodies and/or anti-PD-1 antibodies.

In an alternative second aspect, the invention provides a) a composition comprising hexyl 5-ALA ester (HAL) or a pharmaceutically acceptable salt thereof and b) a composition comprising anti-PD-L1 antibodies and/or anti-PD-1 antibodies, each of which is for use in a neoadjuvant therapy for bladder cancer in a bladder cancer patient who is scheduled for a cystectomy, said neoadjuvant therapy comprises instilling a) into the bladder of said patient and exposing the inside of said bladder to light and instilling b) into the bladder of said patient.

Embodiments and preferred embodiments of the second aspect of the invention are those described in the context of the first aspect of the invention.

Preferred anti-PD-L1 antibodies are those by Roche, preferably MPDL3280A. Said preferred anti-PD-L1 antibodies are described in WO 2010/077634, WO 2013/019906 and WO 2013/181452, the entire contents of which are incorporated herein by reference.

Preferred anti-PD-1 antibodies are those by Merck, preferably pembrolizumab (Keytruda). Such preferred anti-PD-1 antibodies are described in WO 2008/156712, WO 2009/114335 and WO 2013/079174, the entire contents of which are incorporated herein by reference.

Other preferred anti-PD-1 antibodies are those by Bristol-Myers Squibb, preferably nivolumab (Opdivo). Such preferred anti-PD-1 antibodies are described in WO 2004/004771, the entire contents of which are incorporated herein by reference.

The neoadjuvant therapy according to the invention may be carried out prior, subsequently or after a neoadjuvant therapy with anti-PD-L1 antibodies and/or anti-PD-1 antibodies.

Such antibodies may be formulated and administered as described in WO 2010/077634, WO 2013/019906 and WO 2013/181452 (for anti-PD-L1 antibodies) or in WO 2004/004771, WO 2008/156712, WO 2009/114335 and WO 2013/079174 (for anti-PD-1 antibodies), i.e. formulated in a formulation which is suitable for parenteral (e.g. subcutaneous) or intravenous administration. In a preferred embodiment, such anti-PD-L1 antibodies and/or anti-PD-1 antibodies are formulated for instillation into the bladder, preferably as a liquid composition. Preferred liquid compositions are solutions or suspensions of anti-PD-L1 antibodies and/or anti-PD-1 antibodies, i.e. more preferably comprise anti-PD-L1 antibodies and/or anti-PD-1 antibodies in a liquid carrier. Preferred liquid carriers are water or aqueous solutions, most preferably aqueous buffers.

In a preferred embodiment, the anti-PD-L1 antibodies and/or anti-PD-1 antibodies are provided in a lyophilized form, and are reconstituted in a liquid carrier, preferably in water or an aqueous solution, most preferably in an aqueous buffer, prior to use.

If the liquid composition comprises water, the pH of said composition is preferably in the range of 4.5 to 7.5.

In a preferred embodiment, the composition for use in the neoadjuvant therapy of the invention comprises a therapeutically effective amount of anti-PD-L1 antibodies and/or anti-PD-1 antibodies. Such therapeutically effective amount can be administered in one or more instillations into the bladder. For purposes of this invention, a therapeutically effective amount of anti-PD-L1 antibodies and/or anti-PD-1 antibodies is an amount sufficient to accomplish therapeutic treatment together with at least the main treatment, i.e. cystectomy. Other neoadjuvant treatments may be carried out together with the neoadjuvant therapy of the invention, e.g. neoadjuvant radiotherapy, neoadjuvant chemotherapy or neoadjuvant immunotherapy.

After cystectomy, the patient may receive adjuvant chemotherapy with e.g. cisplatin, methotrexate, vinblastine, adriamycin, gemcitabine, doxorubicin, epirubicin, cyclophosphamide or combinations thereof. Alternatively or in addition thereto, the patient may receive adjuvant immunotherapy with e.g. anti-PD-L1 antibodies.

In a third aspect, the invention provides a composition comprising a) hexyl 5-ALA ester (HAL) or a pharmaceutically acceptable salt thereof and b) anti-PD-L1 antibodies and/or anti-PD-1 antibodies for use in the neoadjuvant therapy for bladder cancer in a bladder cancer patient who is scheduled for a cystectomy, said neoadjuvant therapy comprises the instillation of the composition into the bladder of said patient and exposing the inside of said bladder to light.

In an alternative third aspect, the invention provides a neoadjuvant therapy for bladder cancer in a bladder cancer patient who is scheduled for a cystectomy, said therapy comprises instilling into the bladder of said patient a composition comprising a) hexyl 5-ALA ester (HAL) or a pharmaceutically acceptable salt thereof and b) anti-PD-L1 antibodies and/or anti-PD-1 antibodies and exposing the inside of said bladder to light.

Embodiments and preferred embodiments of the third aspect of the invention are those described in the context of the first and second aspect of the invention.

Various embodiments of the invention are as follows:

Embodiment 1

Composition comprising hexyl 5-ALA ester (HAL) or a pharmaceutically acceptable salt thereof for use in a neoadjuvant therapy for bladder cancer in a bladder cancer patient who is scheduled for a cystectomy, the therapy comprises instilling said composition into the bladder of said patient and exposing the inside of said bladder to light.

Embodiment 2

Composition for use according to embodiment 1, wherein the bladder cancer is muscular invasive bladder cancer (MIBC).

Embodiment 3

Composition for use according to embodiment 1, wherein the bladder cancer is non-muscular invasive bladder cancer (NMIBC).

Embodiment 4

Composition for use according to embodiment 3, wherein the bladder cancer is NMIBC with a high risk of progression.

Embodiment 5

Composition for use according to any of the preceding embodiments, wherein the composition comprises a pharmaceutically acceptable salt of HAL.

Embodiment 6

Composition for use according to embodiment 5, wherein the composition comprises the hydrochloride salt of HAL.

Embodiment 7

Composition for use according to any of the preceding embodiments, wherein the composition comprises HAL in the range of 0.1 to 5% by weight of the total weight of the composition or the equivalent concentration of a pharmaceutically acceptable salt of HAL.

Embodiment 8

Composition for use according to any of the preceding embodiments, wherein the composition is a semi-solid composition or a liquid composition.

Embodiment 9

Composition for use according to any of the preceding embodiments, wherein the composition is liquid composition comprising a liquid carrier, preferably water, an aqueous solution or an aqueous buffer, preferably a phosphate buffer.

Embodiment 10

Composition for use according to any of the preceding embodiments, wherein the composition is a liquid composition comprising hexyl 5-ALA ester hydrochloride at a concentration of 0.2% in an aqueous phosphate buffer comprising disodium phosphate dehydrate, potassium dihydrogen phosphate, sodium chloride, hydrochloric acid, sodium hydroxide and water.

Embodiment 11

Composition for use according to any of the preceding embodiments, wherein the composition is instilled into the bladder through a catheter and left in the bladder from about 20 minutes to about 3 hours.

Embodiment 12

Composition for use according to any of the preceding embodiments, wherein at least 1 hour is allowed to pass from the instillation of the composition into the bladder to the start of exposing the inside of the bladder to light.

Embodiment 13

Composition for use according to any of the preceding embodiments, wherein the inside of the bladder is exposed to white light and/or blue light and/or red light.

Embodiment 14

Composition for use according to embodiment 13, wherein the inside of the bladder is exposed to white light followed by blue light.

Embodiment 15

Composition for use according to any of the preceding embodiments, wherein the time between said neoadjuvant therapy and the cystectomy is zero to 6 weeks.

Embodiment 16

Composition for use according to any of the preceding embodiments, wherein said neoadjuvant therapy is carried out prior, simultaneously or after other neoadjuvant therapies.

Embodiment 17

Composition for use according to any of the preceding embodiments, wherein said composition further comprises anti-PD-L1 antibodies and/or anti-PD-1 antibodies.

Embodiment 18

Composition for use according to embodiment 17, wherein said composition comprises anti-PD-L1 antibodies.

Embodiment 19

Composition for use according to embodiment 17, wherein said composition comprises anti-PD-1 antibodies.

Embodiment 20

Composition for use according to embodiment 17 wherein said composition comprises anti-PD-L1 antibodies and. anti-PD-1 antibodies.

Embodiment 21

A neoadjuvant therapy for bladder cancer in a bladder cancer patient who is scheduled for a cystectomy, said therapy comprises instilling into the bladder of said patient a composition comprising hexyl 5-ALA ester (HAL) or a pharmaceutically acceptable salt thereof and exposing the inside of said bladder to light.

Embodiment 22

Neoadjuvant therapy according to embodiment 21, wherein the bladder cancer is muscular invasive bladder cancer (MIBC).

Embodiment 23

Neoadjuvant therapy according to embodiment 21, wherein the bladder cancer is non-muscular invasive bladder cancer (NMIBC).

Embodiment 24

Neoadjuvant therapy according to embodiment 23, wherein the bladder cancer is NMIBC with a high risk of progression.

Embodiment 25

Neoadjuvant therapy according to any of the preceding embodiments, wherein the composition comprises a pharmaceutically acceptable salt of HAL.

Embodiment 26

Neoadjuvant therapy according to embodiment 25, wherein the composition comprises the hydrochloride salt of HAL.

Embodiment 27

Neoadjuvant therapy according to any of the preceding embodiments, wherein the composition comprises HAL in the range of 0.1 to 5% by weight of the total weight of the composition or the equivalent concentration of a pharmaceutically acceptable salt of HAL.

Embodiment 28

Neoadjuvant therapy according to any of the preceding embodiments, wherein the composition is a semi-solid composition or a liquid composition.

Embodiment 29

Neoadjuvant therapy according to any of the preceding embodiments, wherein the composition is liquid composition comprising a liquid carrier, preferably water, an aqueous solution or an aqueous buffer, preferably a phosphate buffer.

Embodiment 30

Neoadjuvant therapy according to any of the preceding embodiments, wherein the composition is a liquid composition comprising hexyl 5-ALA ester hydrochloride at a concentration of 0.2% in an aqueous phosphate buffer comprising disodium phosphate dehydrate, potassium dihydrogen phosphate, sodium chloride, hydrochloric acid, sodium hydroxide and water.

Embodiment 31

Neoadjuvant therapy according to any of the preceding embodiments, wherein the composition is instilled into the bladder through a catheter and left in the bladder from about 20 minutes to about 3 hours.

Embodiment 32

Neoadjuvant therapy according to any of the preceding embodiments, wherein at least 1 hour is allowed to pass from the instillation of the composition into the bladder to the start of exposing the inside of the bladder to light.

Embodiment 33

Neoadjuvant therapy according to any of the preceding embodiments, wherein the inside of the bladder is exposed to white light and/or blue light and/or red light.

Embodiment 34

Neoadjuvant therapy according to embodiment 33, wherein the inside of the bladder is exposed to white light followed by blue light.

Embodiment 35

Neoadjuvant therapy according to any of the preceding embodiments, wherein the time between said neoadjuvant therapy and the cystectomy is zero to 6 weeks.

Embodiment 36

Neoadjuvant therapy according to any of the preceding embodiments, wherein said neoadjuvant therapy is carried out prior, simultaneously or after other neoadjuvant therapies.

Embodiment 37

Neoadjuvant therapy according to any of the preceding embodiments, wherein said composition further comprises anti-PD-L1 antibodies and/or anti-PD-1 antibodies.

Embodiment 38

Neoadjuvant therapy according to embodiment 37, wherein said composition comprises anti-PD-L1 antibodies.

Embodiment 39

Neoadjuvant therapy according to embodiment 37, wherein said composition comprises anti-PD-1 antibodies.

Embodiment 40

Neoadjuvant therapy according to embodiment 37 wherein said composition comprises anti-PD-L1 antibodies and. anti-PD-1 antibodies.

The invention claimed is:

1. A method of neoadjuvant therapy for muscular invasive bladder cancer (MIBC) or non-muscular invasive bladder cancer (NMIBC) with a high risk of progression in a bladder cancer patient who is scheduled for a cystectomy, said method of neoadjuvant therapy comprises:
    instilling into the bladder of said patient who is scheduled for a cystectomy a composition comprising hexyl 5-ALA ester (HAL) or a pharmaceutically acceptable salt thereof; and
    exposing the inside of said bladder to light from a cystoscope;
wherein the time between said neoadjuvant therapy and the cystectomy is zero to 6 weeks.

2. The neoadjuvant therapy according to claim 1, wherein the bladder cancer is muscular invasive bladder cancer (MIBC).

3. The neoadjuvant therapy according to claim 1, wherein the bladder cancer is non-muscular invasive bladder cancer (NMIBC) with a high risk of progression.

4. The neoadjuvant therapy according to claim 1, wherein the composition comprises a pharmaceutically acceptable salt of HAL.

5. The neoadjuvant therapy according to claim 4, wherein the composition comprises the hydrochloride salt of HAL.

6. The neoadjuvant therapy according to claim 1, wherein the composition comprises HAL in the range of 0.1 to 5% by weight of the total weight of the composition or the equivalent concentration of a pharmaceutically acceptable salt of HAL.

7. The neoadjuvant therapy according to claim 1, wherein the composition is a semi-solid composition or a liquid composition.

8. The neoadjuvant therapy according to claim 1, wherein the composition is liquid composition comprising a liquid carrier.

9. The neoadjuvant therapy according to claim 8, wherein the liquid carrier water or an aqueous buffer.

10. The neoadjuvant therapy according to claim 9, wherein the aqueous buffer is a phosphate buffer.

11. The neoadjuvant therapy according to claim 1, wherein the composition is a liquid composition comprising hexyl 5-ALA ester hydrochloride at a concentration of 0.2% in an aqueous phosphate buffer comprising disodium phosphate dehydrate, potassium dihydrogen phosphate, sodium chloride, hydrochloric acid, sodium hydroxide and water.

12. The neoadjuvant therapy according to claim 1, wherein the composition is instilled into the bladder through a catheter and left in the bladder from about 20 minutes to about 3 hours.

13. The neoadjuvant therapy according to claim 1, wherein at least 1 hour is allowed to pass from the instillation of the composition into the bladder to the start of exposing the inside of the bladder to light.

14. The neoadjuvant therapy according claim 1, wherein the inside of the bladder is exposed to white light and/or blue light and/or red light.

15. The neoadjuvant therapy according to claim 14, wherein the inside of the bladder is exposed to white light followed by blue light.

16. The neoadjuvant therapy according to claim 1, wherein said neoadjuvant therapy is carried out prior, simultaneously or after other neoadjuvant therapies.

17. The neoadjuvant therapy according to claim 1, wherein said composition further comprises anti-PD-L1 antibodies and/or anti-PD-1 antibodies.

18. The neoadjuvant therapy according to claim 17, wherein said composition comprises anti-PD-L1 antibodies or anti-PD-1 antibodies.

* * * * *